(12) United States Patent
Ma et al.

(10) Patent No.: US 11,992,060 B2
(45) Date of Patent: May 28, 2024

(54) ATOMIZER AND ELECTRONIC ATOMIZATION DEVICE

(71) Applicant: Shenzhen Smoore Technology Limited, Shenzhen (CN)

(72) Inventors: Jie Ma, Shenzhen (CN); Yinlong Lan, Shenzhen (CN); Weijin Huang, Shenzhen (CN); Weiguang Hu, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 343 days.

(21) Appl. No.: 17/384,785

(22) Filed: Jul. 25, 2021

(65) Prior Publication Data
US 2022/0053835 A1     Feb. 24, 2022

(30) Foreign Application Priority Data
Aug. 18, 2020  (CN) .......................... 202021744378.X (51) Int. Cl.
| | |
|---|---|
| *A24F 40/49* | (2020.01) |
| *A24F 7/02* | (2006.01) |
| *A24F 40/10* | (2020.01) |
| *A24F 40/42* | (2020.01) |
| *A24F 40/485* | (2020.01) |

(52) U.S. Cl.
CPC ................ *A24F 40/49* (2020.01); *A24F 7/02* (2013.01); *A24F 40/10* (2020.01); *A24F 40/42* (2020.01); *A24F 40/485* (2020.01)

(58) Field of Classification Search
CPC ........ A24F 40/10; A24F 40/42; A24F 40/485; A24F 40/49; A24F 7/02
See application file for complete search history.

(56) References Cited

FOREIGN PATENT DOCUMENTS

| | | | |
|---|---|---|---|
| CN | 203446538 U | 2/2014 | |
| CN | 207236094 U | 4/2018 | |
| CN | 209185764 U | 8/2019 | |
| CN | 111134370 A | * 5/2020 | ............. A24F 40/40 |

(Continued)

OTHER PUBLICATIONS

CN111134370A_Machine Translation (Year: 2020).*

(Continued)

*Primary Examiner* — Christopher M Rodd
*Assistant Examiner* — Ronnie Kirby Jordan (57) ABSTRACT

An atomizer includes: a liquid storage assembly, including an inner barrel, wherein the inner barrel defines a slide cavity, the slide cavity is defined for receiving the atomization core assembly; and a mouthpiece assembly, disposed at an end of the inner barrel for pushing against the atomization core assembly, such that the atomization core assembly slides relative to the inner barrel, and an end of the atomization core assembly is exposed to an outside of the atomizer. By configuring the mouthpiece assembly to push against the atomization core assembly, the atomization core assembly slides along the slide cavity of the inner barrel, and one end of the atomization core assembly is exposed to the outside. Therefore, it may be difficult for children to disassemble the atomizer core assembly, a risk of children removing the atomization core assembly and causing hazards to themselves may be reduced effectively.

20 Claims, 9 Drawing Sheets

(56) References Cited

FOREIGN PATENT DOCUMENTS

| EP | 3406146 A1 | * | 11/2018 | ............. | A24F 40/00 |
| WO | WO2018086443 A1 | | 5/2018 | | |
| WO | WO2018120203 A1 | * | 7/2018 | ............. | A24F 40/30 |
| WO | WO2019174635 A1 | | 9/2019 | | |

OTHER PUBLICATIONS

WO2018120206A1_Machine Translation (Year: 2018).*
European search report, European Application No. 21191416.3, mailed 01.14.2022 (6 pages).
First correction notice, Chinese Application No. 202021744378.X, mailed 06.07.2021 (2 pages).
European Examination Report, European Application No. 21191416.3, mailed Sep. 4, 2023 (4 pages).

* cited by examiner

ATOMIZER AND ELECTRONIC ATOMIZATION DEVICE

CROSS REFERENCE TO RELATED APPLICATIONS

The present application claims the foreign priority of the Chinese Patent Application No. 202021744378.X filed on Aug. 18, 2020, and the entire content of which is hereby incorporated by reference in its entirety.

TECHNICAL FIELD

The present disclosure relates to the field of atomization, and in particular to an atomizer and an electronic atomization device.

BACKGROUND

An electronic atomization device in the art generally includes an atomizer and a battery. An atomization core may be configured inside the atomizer. The atomization core may heat and atomize a substrate. The atomization core has a service life. When the user needs to replace the atomization core in the atomizer, the user may need to rotate to disengage a connection structure and remove the atomization core or directly pull out the atomization core.

However, this is a simple way to remove the atomization core, which makes it possible for children to open the atomizer and contact the substrate therein, and can result in accidental ingestion of the substrate.

SUMMARY OF THE DISCLOSURE

The present application provides an atomizer and an electronic atomization device to solve the problem that the atomization core may be easily disassembled from the atomizer and harmful to vulnerable people, such as children.

According to an aspect of the present disclosure, an atomizer is provided. The atomizer includes: a liquid storage assembly and a mouthpiece assembly. The atomizer includes an inner barrel, and the inner barrel defines a slide cavity for receiving an atomization core assembly. The mouthpiece assembly is disposed at an end of the inner barrel for pushing against the atomization core assembly, the atomization core assembly is capable of sliding relative to the inner barrel, and an end of the atomization core assembly is capable of being exposed to an outside of the atomizer.

According to another aspect of the present disclosure, an electronic atomization device is provided and includes a body assembly and the atomizer as described in the above. The body assembly is connected to the atomizer and is configured to supply power for the atomizer.

According to still another aspect of the present disclosure, an atomizer is provided and includes an atomization core assembly, a liquid storage assembly, and a mouthpiece assembly. The atomization core assembly is configured to atomize liquid. The liquid storage assembly defines a receiving channel, and the atomization core assembly is received in the receiving channel. The mouthpiece assembly is disposed at a first end of the liquid storage assembly. The mouthpiece assembly is configured to push the atomization core assembly to slide the atomization core assembly in the receiving channel, and an end of the atomization core assembly is capable of being exposed to an outside of the atomizer through a second end of the liquid storage assembly opposite to the first end.

BRIEF DESCRIPTION OF THE DRAWINGS

In order to more clearly illustrate technical solutions in the embodiments of the present application or in the prior art, a brief description of the accompanying drawings used in the embodiments or in the prior art is provided. Obviously, the drawings in the following description are only some embodiments of the present disclosure, and for a person of ordinary skill in the art, other drawings may be obtained from these drawings without any creative effort.

DETAILED DESCRIPTION

The technical solutions in the embodiments of the present disclosure will be clearly and completely described by referring to the accompanying drawings in the embodiments of the present disclosure. Obviously, the described embodiments are only a part of, but not all of, the embodiments of the present disclosure. Based on the embodiments in the present disclosure, all other embodiments obtained by a person of ordinary skill in the art without making creative work shall fall within the scope of the present disclosure.

The terms "first", "second" and "third" in the embodiments of the present disclosure are used for descriptive purposes only and should not be interpreted as indicating or implying relative importance of the indicated technical features or implicitly specifying the number of the technical features. Therefore, a feature defined by the "first," "second," or "third" may explicitly or implicitly include at least one such feature. In the description of the present disclosure, "plurality" means at least two, such as two, three, etc., unless otherwise expressively and specifically limited. In addition, the terms "includes" and "has", and any variations thereof, are intended to cover non-exclusive inclusion. For example, a process, a method, a system, a product or an apparatus including a series of operations or units is not limited to the listed operations or units, but optionally also includes operations or units that are not listed, or optionally also includes other operations or units that are inherent to the process, the method, the product or the apparatus.

References to "embodiments" mean that a particular feature, structure, or characteristic described by referring to an embodiment may be included in at least one embodiment of the present disclosure. The presence of the term at various sections in the specification does not necessarily mean a same embodiment, nor is it a separate or alternative embodiment that is mutually exclusive with other embodiments. It is understood, both explicitly and implicitly, by the skilled person in the art that the embodiments described herein may be combined with other embodiments.

Figure 1:
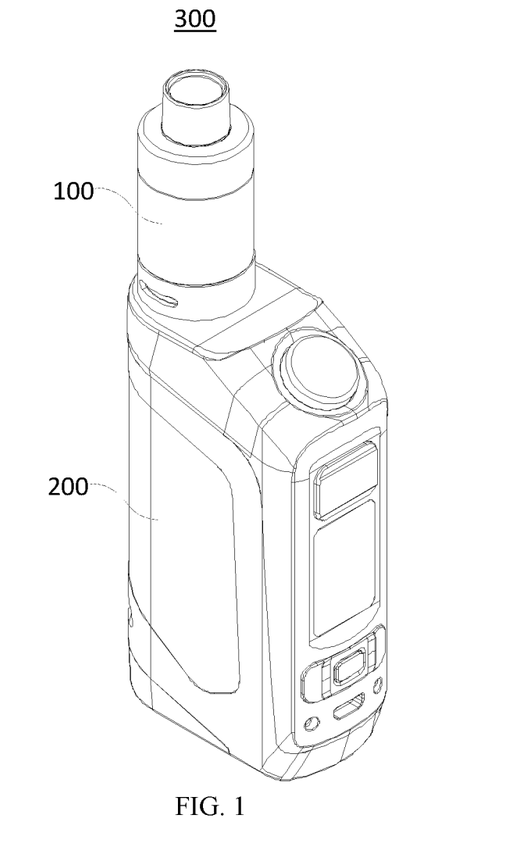
FIG. 1 is a structural schematic view of an electronic atomization device according to an embodiment of the present disclosure.
Figure 2:
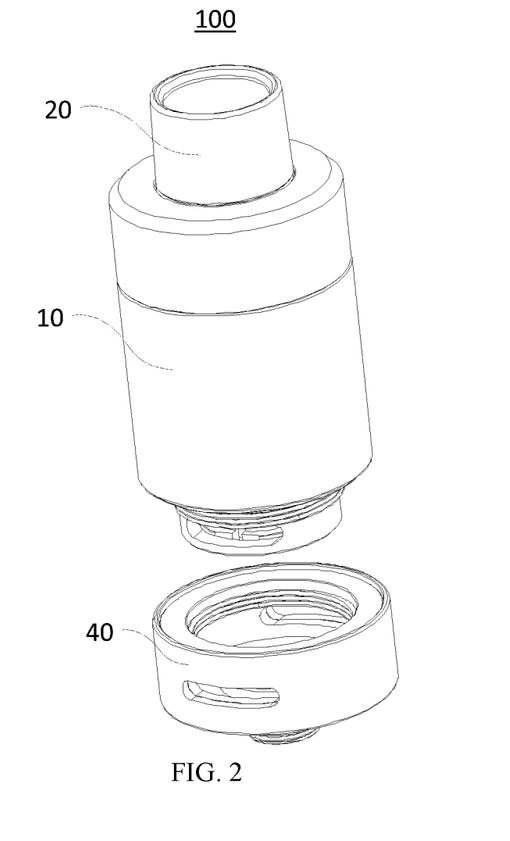
FIG. 2 is a structural schematic view of an atomizer of the electronic atomization device shown in FIG. 1.
Figure 3:
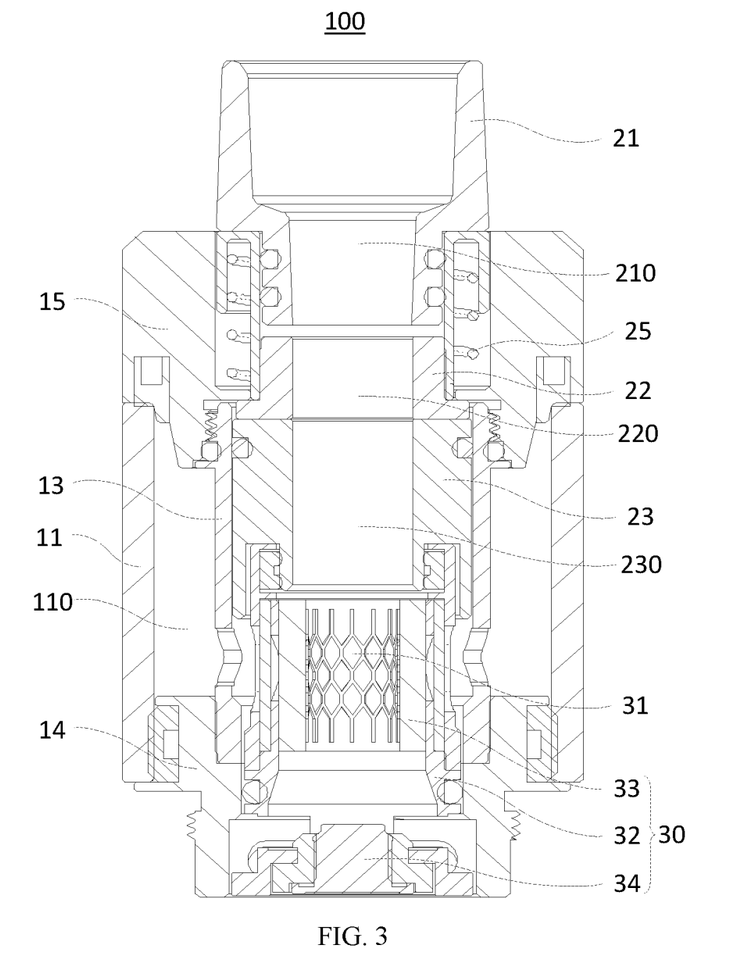
FIG. 3 is a cross-sectional view of the atomizer shown in FIG. 2.
Figure 4:
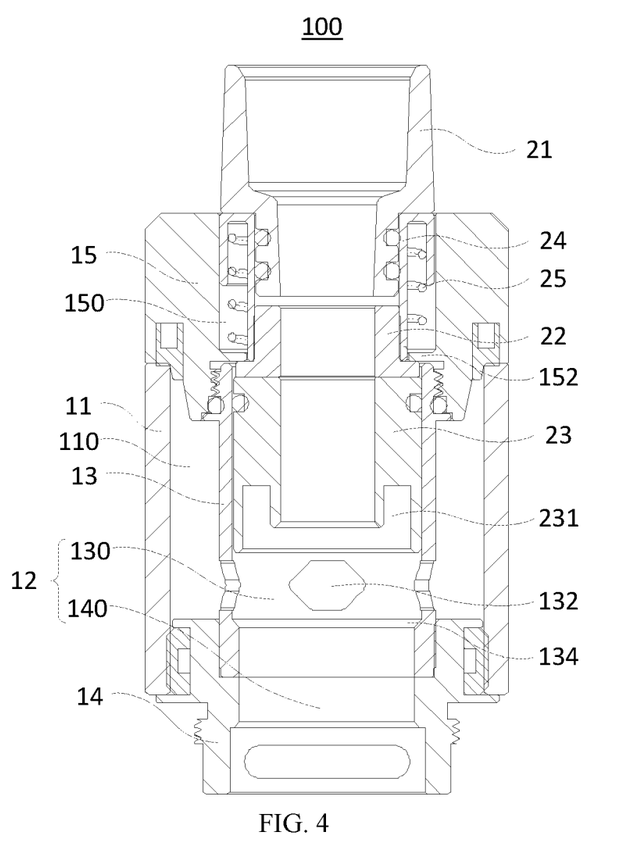
FIG. 4 is a cross-sectional view of the atomizer shown in FIG. 3 with an atomization core assembly omitted.

The present disclosure provides an electronic atomization device 300, shown in FIGS. 1 to 4. FIG. 1 is a structural schematic view of an electronic atomization device according to an embodiment of the present disclosure. FIG. 2 is a structural schematic view of an atomizer of the electronic atomization device shown in FIG. 1. An end cap assembly 40 of the atomizer shown in FIG. 2 may be in a separated state from a liquid storage assembly 10. FIG. 3 is a cross-sectional view of the atomizer shown in FIG. 2. FIG. 4 is a cross-sectional view of the atomizer shown in FIG. 3 with an atomization core assembly omitted.

The electronic atomization device 300 may be configured to atomize an e-liquid. As shown in FIG. 1, the electronic atomization device 300 may include an atomizer 100 and a body assembly 200, connected with each other. The atomizer 100 may be configured to store a liquid and atomize the liquid to generate smoke that can be inhaled by a user. The liquid may be liquid matrix, such as an e-liquid, a medicinal liquid, and the like. The body assembly 200 may be configured to supply power for the atomizer 100 to enable the atomizer 100 to atomize the e-liquid to generate the smoke.

In the present embodiment, the e-liquid may be taken as an example for illustration.

As shown in FIGS. 2 to 4, the atomizer 100 may include a liquid storage assembly 10, a mouthpiece assembly 20, an atomizer core assembly 30, and an end cap assembly 40. The liquid storage assembly 10 may be configured to store the e-liquid and may define a receiving channel 12. The atomizer core assembly 30 may be received in the receiving channel 12. The atomizer core assembly 30 may be configured to atomize the e-liquid to generate the smoke. The mouthpiece assembly 20 may be connected to the liquid storage assembly 10. Cavities of the mouthpiece assembly 20, the liquid storage assembly 10, and the atomization core assembly 30 may be communicated with each other, such that the user may inhale the smoke generated by the atomization core assembly 30 through the mouthpiece assembly 20. The end cap assembly 40 may be connected to an end of the liquid storage assembly 10 opposite to the mouthpiece assembly 20. The end cap assembly 40 may cover the receiving channel 12.

The liquid storage assembly 10 may include an outer barrel 11, an inner barrel 13, a base 14 and a top cover 15. The base 14 and the top cover 15 may be connected to the two ends of the outer barrel 11. The outer barrel 11 may sleeve the inner barrel 13 and may be connected between the base 14 and the top cover 15. A liquid storage cavity 110 may be defined between the outer barrel 11 and the inner barrel 13. The liquid storage cavity 110 may be defined to store the e-liquid.

As shown in FIG. 4, the inner barrel 13 defines a slide cavity 130. An end of the inner barrel 13 away from the mouthpiece assembly 20 is provided with the base 14. The base 14 may define an embedding channel 140. The slide cavity 130 and the embedding channel 140 are communicated. The receiving channel 12 may include the slide cavity 130 and the embedding channel 140. The atomization core assembly 30 may be entirely received in the slide cavity 130 and the embedding channel 140.

In other embodiments, the base 14 sleeves an outer periphery of the inner barrel 13 and limits a position of the inner barrel 13 along an axial direction. The slide cavity 130 may serve as the receiving channel 12, and the atomization core assembly 30 may be entirely received in the slide cavity 130. Alternatively, the top cover 15 may define a receiving chamber, and the slide cavity 130 may be communicated with the receiving chamber. The slide cavity 130 and the receiving chamber may cooperatively serve as the receiving channel 12. Alternatively, the embedding channel 140, the slide cavity 130 and the receiving chamber of the top cover 15 may cooperatively serve as the receiving channel 12.

In the present disclosure, the liquid storage assembly 10 defines the receiving channel 12. The receiving channel 12 may be defined to receive the entire atomization core assembly 30, that is, all components of the atomization core assembly 30 may be received in the receiving channel 12. The atomization core assembly 30 is received in the receiving channel 12 in a drop-preventing manner. In other words, the atomization core assembly 30 may not slide in the receiving channel 12 arbitrarily to be released from the receiving channel 12. A size of an end of the receiving channel 12 may match with a size of an end of the atomization core assembly 30. That is, the size of the end of the receiving channel 12 may approximately be the same as the size of the end of the atomization core assembly 30. Therefore, children may not be able to use fingers to reach an inside of the receiving channel 12 and pull the atomization core assembly 30. The children may be prevented from accidentally separating the atomization core assembly 30 from the receiving channel 12, causing the e-liquid to leak. The occurrence of the children accidentally contacting and ingesting the e-liquid may be reduced.

As shown in FIG. 3, the atomization core assembly 30 may include a substrate 32, an atomization element 33 and an electrode 34. The atomization element 33 and the electrode 34 may be mounted on the substrate 32. The electrode 34 may be electrically connected to the atomization element 33. The atomization element 33 may include a liquid guiding member and an atomization member. The liquid guiding member may be liquid guiding cotton or liquid guiding fiber, and the like. The atomization member may be a heating mesh or a resistance wire, and the like. The atomization member may be electrically connected to the electrode. The atomization member may be configured to atomize the e-liquid guided by the liquid guiding member. The atomization element 33 may be porous ceramic silicon, which will not be limited by the present disclosure.

As shown in FIGS. 2 to 4, the end cap assembly 40 may be connected to the base 14. The end cap assembly 40 may seal the receiving channel 12 to cover the atomization core assembly 30, such that the children may be protected from contacting the atomization core assembly 30.

In the present embodiment, a thread may be configured at an outer circumference of the base 14. The end cap assembly 40 and the base 14 may be threadedly connected. The atomization core assembly 30 may be electrically connected to the end cap assembly 40, and power may be supplied to the atomization core assembly 30 through the end cap assembly 40. Specifically, the end cap assembly 40 may include an electrode. After the end cap assembly 40 is connected to the base 14, the electrode of the end cap assembly 40 may be electrically connected to the electrode 34 of the atomization core assembly 30.

Therefore, the end cap assembly 40 may further be configured to connect to the base 14 and cover the atomization core assembly 30 to further isolate the atomization core assembly 30, such that the children may be protected from accidentally operating the device, causing the e-liquid to leak, and protected from accidentally ingesting the e-liquid.

In other embodiments, the atomizer 100 may not include the end cap assembly 40, and the structure of the atomizer 100 shown in FIG. 3 may be applied.

In the present embodiment, as shown in FIG. 4, both the base 14 and the top cover 15 may be detachably connected to the outer barrel 11, and both the base 14 and the top cover 15 may be detachably connected to the inner barrel 13. For example, the connection may be thread connection or buckled connection via a sealing member, and the like. In other embodiments, the top cover 15, the outer barrel 11 and the inner barrel 13 may be configured as an integral overall structure. Alternatively, the base 14, the outer barrel 11 and the inner barrel 13 may be configured as an integral overall structure. Alternatively, the top cover 15 and the inner barrel 13 may be configured as an integral overall structure. The present disclosure does not limit the integrity of the above components.

The top cover 15 may define a guide cavity 150. An internal thread may be configured at an end of the top cover 15 facing the inner barrel 13. An external thread may be configured on an outer circumference of the inner barrel 13. The top cover 15 may be threadedly connected to the inner barrel 13. The mouthpiece assembly 20 may be configured at an end of the inner barrel 13, extend through the guide cavity 150, and may be guided by the guide cavity 150. A cavity of the mouthpiece assembly 20 may be communicated with an atomization chamber 31 in the atomization core assembly 30, such that the user may inhale the smoke in the atomization chamber 31 through the mouthpiece assembly 20.

In the present disclosure, the mouthpiece assembly 20 may further be configured to abut against and push the atomizer core assembly 30, such that the atomizer core assembly 30 may slide relative to the inner barrel 13, and an end of the atomizer core assembly 30 may be exposed to an outside from the end of the receiving channel 12. In this way, the atomizer core assembly 30 may be released from the receiving channel 12 by pulling the exposed end of the atomizer core assembly 30.

The atomizer 100 may further include an elastic member 25. An end of the elastic member 25 may abut against the mouthpiece assembly 20. The elastic member 25 may be elastically compressed while the mouthpiece assembly 20 pushes against the atomizer core assembly 30. The compressed elastic member 25 may be configured to push against the mouthpiece assembly 20 to reset, after an external force applied on the mouthpiece assembly 20 is removed.

The elastic member 25 may be a spring or an elastic sleeve, and the like.

The mouthpiece assembly 20 may include a mouthpiece 21, a stop sleeve 22 and a slide sleeve 23. An end of the elastic member 25 may abut against the mouthpiece 21. An end of the stop sleeve 22 may be connected to the mouthpiece 21. The other end of the stop sleeve 22 may be configured to be stopped to limit a position of the stop sleeve 22 when the mouthpiece 21 is reset. The slide sleeve 23 may be received in the slide cavity 130 and may be detachably connected to the atomization core assembly 30. The mouthpiece 21 may be driven by an external force to drive the stop sleeve 22 to push against the slide sleeve 23, such that the end of the atomization core assembly 30 may be exposed to the outside from the end of the receiving channel 12. After separating the atomization core assembly 30 and the slide sleeve 23, the elastic member 25 may provide elasticity to reset the mouthpiece 21 and the stop sleeve 22.

As shown in FIG. 3, the mouthpiece 21 may define a first smoke channel 210, the stop sleeve 22 may define a second smoke channel 220, and the slide sleeve 23 may define a third smoke channel 230. The first smoke channel 210, the second smoke channel 220, the third smoke channel 230 and the atomization chamber 31 may be communicated. The smoke generated in the atomization chamber 31 may successively flow through the third smoke channel 230, the second smoke channel 220 and the first smoke channel 210, reaching an oral of the user.

As shown in FIG. 4, in the present embodiment, a stop ring 152 may be configured on an inner wall of the guide cavity 150. The elastic member 25 may be elastically compressed between the mouthpiece 21 and the stop ring 152. The mouthpiece 21 may extend and retract along the guide cavity 150. The stop sleeve 22 may extend through the stop ring 152. The other end of the stop sleeve 22 may be disposed on a side of the stop ring 152 away from the elastic member 25 and may be engaged with the stop ring 152 for position-limiting.

Figure 5:
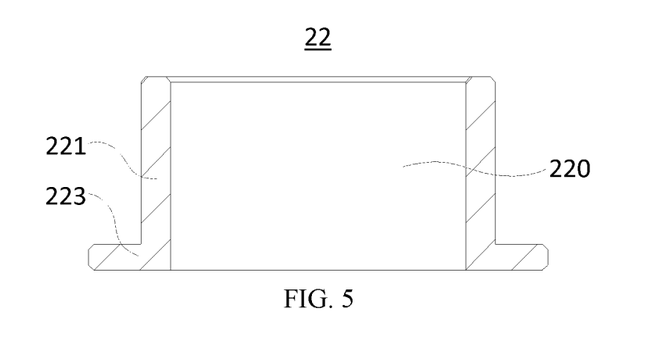
FIG. 5 is a cross-sectional view of a stop sleeve of the atomizer shown in FIG. 4.

As shown in FIG. 5, the stop sleeve 22 may include a sleeve body 221 and a limitation ring 223 disposed on an outer circumference of the sleeve body 221. An end of the sleeve body 221 may be connected to the mouthpiece 21. The other end of the sleeve body 221 may be configured with the limitation ring 223. The sleeve body 221 may extend through the stop ring 152. The limitation ring 223 and the mouthpiece 21 may be disposed on two sides of the stop ring 152, the limitation ring 223 and the stop ring 152 may be engaged for position-limiting.

In other embodiments, an end of the inner barrel 13 facing the mouthpiece 21 and located in the slide cavity 130 may be configured with the stop ring 152, such that the end of the inner barrel 13 facing the mouthpiece 21 may stop and limit the position of the other end of the stop sleeve 22.

As shown in FIG. 4, in the present embodiment, a sealing member may be disposed between the slide sleeve 23 and the inner barrel 13. The sealing member may be a seal ring or a seal rib. In this way, the slide sleeve 23 may be received in the slide cavity 130 in a drop-preventing manner. The atomization core assembly 30 may be connected to the slide sleeve 23, such that the atomization core assembly 30 may be received in the slide cavity 130 through the slide sleeve 23 in a drop-preventing manner.

The stop sleeve 22 and the slide sleeve 23 may be independent of each other. The stop sleeve 22 may push against the slide sleeve 23 to slide along the slide cavity 130. A position of the slide sleeve 23 relative to the inner barrel 13 may remain unchanged when the mouthpiece 21 and the stop sleeve 22 are reset.

A side wall of the inner barrel 13 may define a liquid inlet hole 132. The slide sleeve 23 may be staggered with the liquid inlet hole 132 when the atomizer core assembly 30 is received in the receiving channel 12, such that the e-liquid in the liquid storage cavity 110 may enter the atomizer core assembly 30 through the liquid inlet hole 132 to be atomized. When the slide sleeve 23 pushes the atomizer core assembly 30 to expose the end of the atomizer core assembly, an outer wall of the slide sleeve 23 may cover the liquid inlet hole 132 to prevent the e-liquid in the liquid storage cavity 110 from leaking into the slide cavity 130. Therefore, the e-liquid in the liquid storage cavity 110 may not leak even when the atomizer core assembly 30 is detached from the receiving channel 12. The outer wall of the slide sleeve 23 maintains covering the liquid inlet hole 132 while the mouthpiece 21 and stop sleeve 22 are reset.

In some embodiments, the slide sleeve 23 may be connected to the stop sleeve 22. That is, the slide sleeve 23 moves as the stop sleeve 22 moves. The atomization core assembly 30 may be connected to the slide sleeve 23, thus the atomization core assembly 30 may be received in the slide cavity 130 in a relatively drop-preventing manner. Alternatively, the slide sleeve 23 and the stop sleeve 22 may be configured as an integrated connective structure, which is not limited by the present disclosure.

As shown in FIG. 4, in the present embodiment, a protrusion 134 may be configured at an inner wall of an end of the slide cavity 130 of the inner barrel 13 away from the mouthpiece assembly 20. The protrusion 134 may be configured to resist the slide sleeve 23, preventing the slide sleeve 23 from being released from the slide cavity 130 and facilitating the atomizer assembly 30 to separate from the slide sleeve 23.

In another embodiment, as shown in FIG. 4, an end of the inner barrel 13 may be inserted into the base 14, and the base 14 covers the end of the inner barrel 13. In this way, the base 14 may further be configured to resist the slide sleeve 23 to prevent the slide sleeve 23 from being released from the slide cavity 130 through the end of the receiving channel 12. Further, the base 14 may provide a pushing force to the slide sleeve 23 to facilitate the atomizer assembly 30 to separate from the slide sleeve 23.

Figure 6:
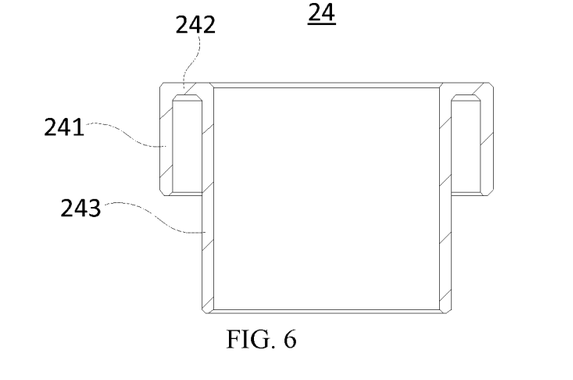
FIG. 6 is a cross-sectional view of a connection sleeve of the atomizer shown in FIG. 4.

As shown in FIG. 4 and FIG. 6, in the present embodiment, the mouthpiece assembly 20 may further include a connection sleeve 24, and the mouthpiece 21 and the stop sleeve 22 may be indirectly connected through the connection sleeve 24. The connection sleeve 24 may include a guide sleeve body 241 and a connection sleeve body 243 sleeving the guide sleeve body 241. The guide sleeve body 241 and the connection sleeve body 243 may be connected through an end plate 242. The mouthpiece 21 and the stop sleeve 22 may be received in two ends of the connection sleeve body 243. An end of the elastic member 25 may abut against the end plate 242. The elastic member 25 may be elastically compressed between the end plate 242 and the stop ring 152. The guide sleeve body 241 may be slidably guided and received in the guide cavity 150 to ensure that the mouthpiece assembly 20 slides in a straight line along the guide cavity 150.

As shown in FIG. 6, the connection sleeve body 243 may be in a shape of a straight barrel.

Figure 9:
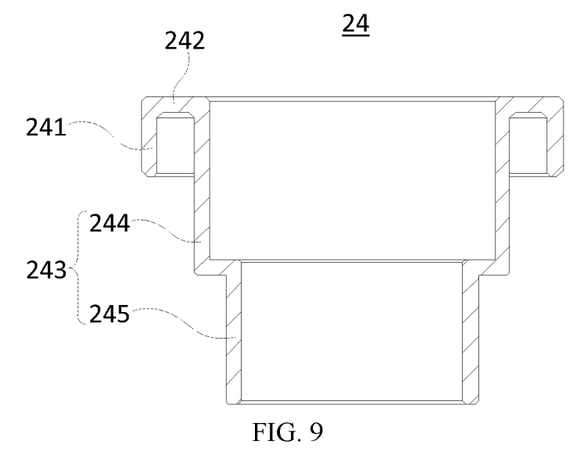
FIG. 9 is a structural schematic view of a connection sleeve of the atomizer shown in FIG. 8.

As shown in FIG. 9, in another embodiment, the connection sleeve body 243 may include a first barrel section 244 and a second barrel section 245, connected to each other. An inner diameter of the first barrel section 244 may be greater than an inner diameter of the second barrel section 245. The mouthpiece 21 may be received in the first barrel section 244, and the stop sleeve 22 may be embedded in the second barrel section 245, such that a radius of the stop sleeve 22 may be reduced along a radial direction. Correspondingly, a radius of the slide sleeve 23 may be reduced along the radial direction. Further, a radius of the inner barrel 13 may also be reduced along the radial direction. In this way, a volume of the liquid storage cavity 110 may be relatively increased, such that more e-liquid may be stored in the liquid storage cavity 110.

In other embodiments, the mouthpiece 21 and the stop sleeve 22 may be directly connected without the connection sleeve 24, such that the elastic member 25 may be directly elastically compressed between the mouthpiece 21 and the stop ring 152.

As shown in FIG. 4, an end of the slide sleeve 23 facing the atomization core assembly 30 may define an insertion slot 231. An end of the atomization core assembly 30 may be inserted in the insertion slot 231. In this way, the atomization core assembly 30 may be assembled in a drop-preventing manner by being received in the receiving channel 12. The atomization core assembly 30 may also be inserted to the slide sleeve 23 or connected to the slide sleeve 23 via a buckle, and the like.

Figure 7:
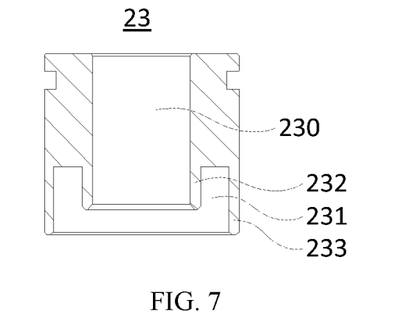
FIG. 7 is a cross-sectional view of a slide sleeve of the atomizer shown in FIG. 4.

Specifically, as shown in FIG. 7, the end of the slide sleeve 23 facing the atomization core assembly 30 may be provided with an inner barrel wall 232 and an outer barrel wall 233, and an axis of the inner barrel wall 232 may be parallel to an axis of the outer barrel wall 233. The insertion slot 231 may be defined between the inner barrel wall 232 and the outer barrel wall 233. An end of the atomization core assembly 30 may be received between the inner barrel wall 232 and the outer barrel wall 233. The atomization core assembly 30 may be embedded between the inner barrel wall 232 and/or the outer barrel wall 233 with an elastic seal member, thereby enabling the atomization core assembly 30 to be connected to the slide sleeve 23.

In other embodiments, the atomization core assembly 30 may be inserted into the slide sleeve 23 or connected to the slide sleeve 23 through a buckle. Alternatively, the atomization core assembly 30 may be threaded to the slide sleeve 23. The present disclosure does not limit the connection therebetween.

As shown in FIG. 7, the slide sleeve 23 may be in a shape of a straight barrel.

Figure 10:
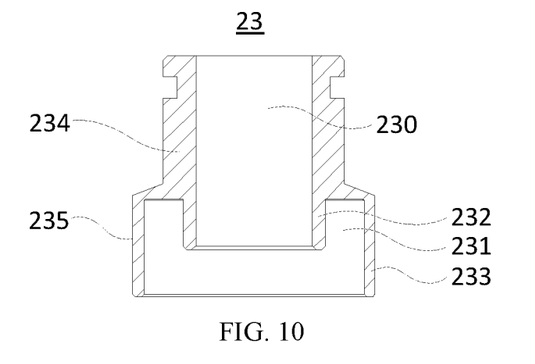
FIG. 10 is a structural schematic view of a slide sleeve of the atomizer shown in FIG. 8.

As shown in FIG. 10, in another embodiment, the slide sleeve 23 may include a first slide sleeve section 234 and a second slide sleeve section 235, connected to each other. An outer diameter of the first slide sleeve section 234 may be less than an outer diameter of the second slide sleeve section 235. An end of the second slide sleeve section 235 away from the first slide sleeve section 234 may define the insertion slot 231. Therefore, a radius of the slide sleeve 23 may be reduced gradually, such that the radius of the inner barrel 13 may be reduced, and the volume of the liquid storage cavity 110 may be increased.

Figure 8:
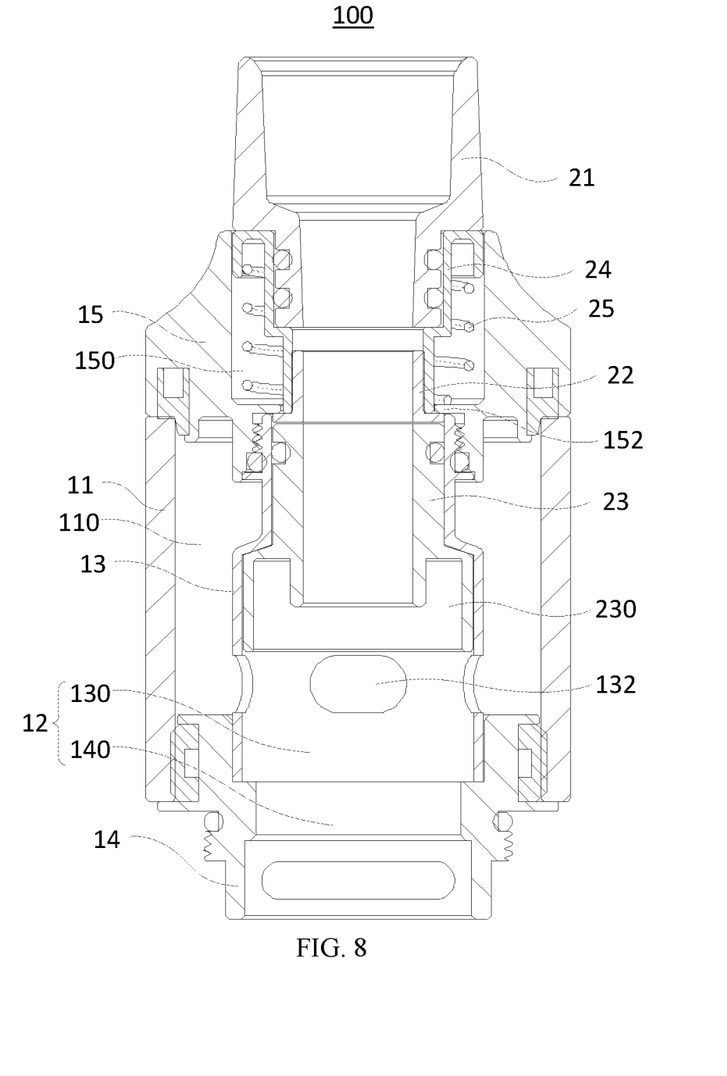
FIG. 8 is another cross-sectional view of the atomizer shown in FIG. 3 with the atomization core assembly omitted.

FIG. 8 is another cross-sectional view of the atomizer shown in FIG. 2. The atomizer 100 shown in FIG. 8 may be obtained by optimizing the atomizer 100 shown in FIG. 4. FIG. 9 is a structural schematic view of the connection sleeve of the atomizer shown in FIG. 8. FIG. 10 is a structural schematic view of the slide sleeve of the atomizer shown in FIG. 8.

By optimizing the stop sleeve 22, the connection sleeve 24 and the slide sleeve 23, the volume of the liquid storage cavity 110 may be effectively increased, such that increased amount of e-liquid may be stored in the liquid storage cavity 110.

Figure 11:
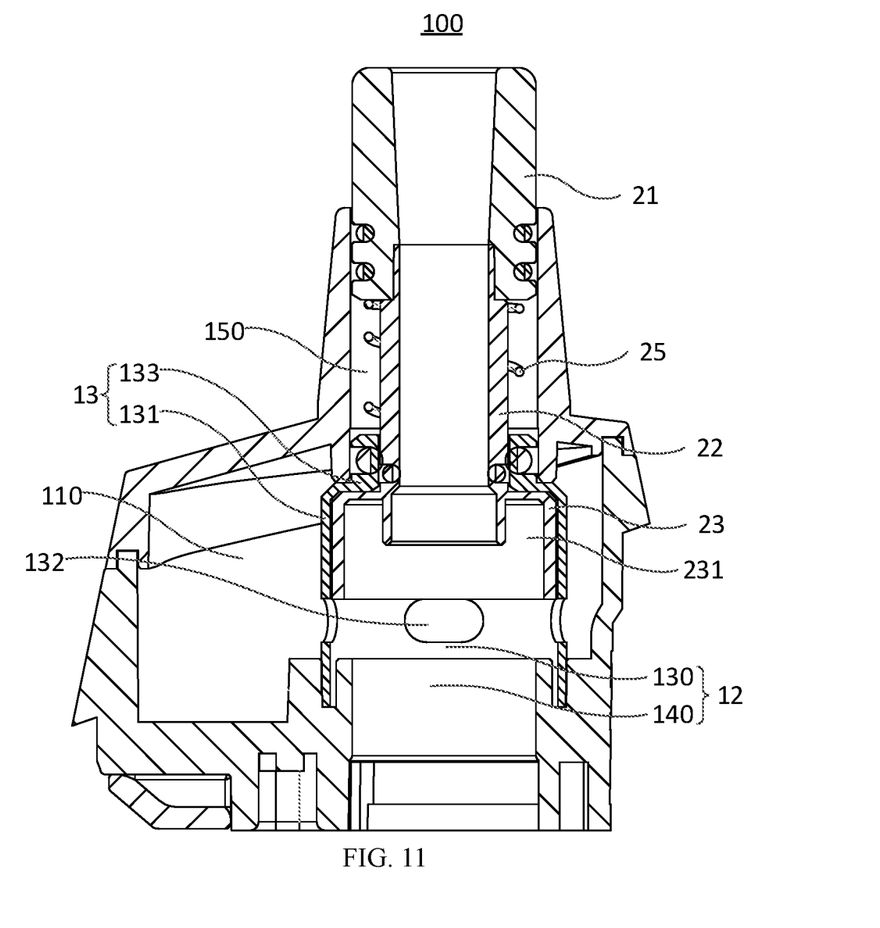
FIG. 11 is another structural schematic view of the atomizer of the electronic atomization device shown in FIG. 1.
Figure 12:
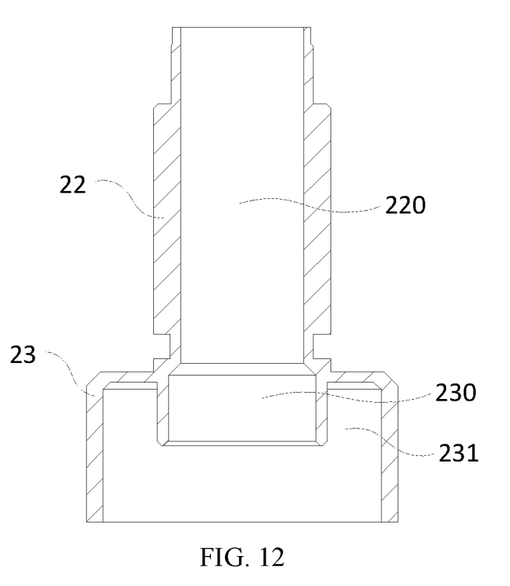
FIG. 12 is a structural schematic view of a stop sleeve and a slide sleeve of the atomizer shown in FIG. 11 configured as an integral overall structure.

FIG. 11 is another structural schematic view of the atomizer of the electronic atomization device shown in FIG. 1. FIG. 12 is a structural schematic view of a stop sleeve and a slide sleeve of the atomizer shown in FIG. 11 configured as an integral overall structure. The atomizer 100 does not include the end cap assembly 40, and the entire atomization core assembly 30 is received in the receiving channel 12.

In the atomizer 100, the inner barrel 13 may be inserted into the guide cavity 150 of the top cover 15 and may abut against an end of the guide cavity 150. The mouthpiece 21 may be slidably received into the guide cavity 150 and sealed by a seal member. The elastic member 25 may be elastically compressed between the mouthpiece 21 and the inner barrel 13. The stop sleeve 22 and the slide sleeve 23 may be connected integrally, that is, the stopper sleeve 22 and the slide sleeve 23 may be an integral overall structure. An end of the stop sleeve 22 may be inserted with the mouthpiece 21.

Specifically, the inner barrel 13 may include a barrel body 131 and a ring stop portion 133 disposed at an end of the barrel body 131. The ring stop portion 133 may further extend into the guide cavity 150. The ring stop portion 133 may be sealed with the guide cavity 150. The elastic member 25 may be elastically compressed between the mouthpiece 21 and the ring stop portion 133. The other end of the stop sleeve 22 may be arranged on a side of the ring stop portion 133 away from the elastic member 25 and may be engaged with the ring stop portion 133 in a position-limiting manner.

By configuring the stop sleeve 22 and the slide sleeve 23 as an integral overall structure, a process of manufacturing the stop sleeve 22 and the slide sleeve 23 may be simplified, and manufacturing costs may be reduced. A process of assembling the atomizer 100 may be further simplified.

The present disclosure provides an atomizer and an electronic atomization device. An atomization core assembly may be received in a slide cavity of an inner barrel, and a mouthpiece assembly may be configured to abut against and push the atomization core assembly to slide atomization core assembly along the slide cavity of the inner barrel, such that an end of the atomization core assembly may be exposed to an outside. The user may remove the atomization core assembly from the atomizer by holding the exposed end of the atomization core assembly. In this way, when the end of the atomization core assembly is not exposed, the user may not take out the atomization core assembly, which may effectively reduce the occurrence of children and other vulnerable people taking off the atomization core assembly, causing hazards to themselves. Therefore, special skills may be required to dissemble the atomization core assembly from the atomizer provided in the present disclosure, which increases difficulty for children and other vulnerable people to disassemble the atomization core assembly, and effectively reduce the occurrence of children and other vulnerable people easily taking out the atomization core assembly and causing hazards to themselves.

The above shows only examples of the present disclosure and is not intended to limit the scope of the present disclosure. Any equivalent structure or equivalent process transformation based on the description and the accompanying drawings of the present disclosure, applied in other related arts directly or indirectly, shall be included in the scope of the present disclosure.

What is claimed is:

1. An atomizer, comprising:
   a liquid storage assembly, comprising an inner barrel, wherein the inner barrel defines a slide cavity for receiving an atomization core assembly; and
   a mouthpiece assembly, disposed at an end of the inner barrel for pushing against the atomization core assembly, wherein the atomization core assembly is capable of sliding relative to the inner barrel when being pushed by the mouthpiece assembly, and an end of the atomization core assembly is capable of being exposed to an outside of the atomizer when being pushed by the mouthpiece assembly; and
   an elastic member;
   wherein the mouthpiece assembly comprises:
   a mouthpiece, wherein an end of the elastic member abuts against the mouthpiece;
   a stop sleeve, wherein an end of the stop sleeve is connected to the mouthpiece, and the other end of the stop sleeve is arranged with a flange configured to prevent the stop sleeve from being moved when the mouthpiece is reset; and
   a slide sleeve, received in the slide cavity and detachably connected to the atomization core assembly.

2. The atomizer according to claim 1, wherein the elastic member is elastically compressed when the mouthpiece assembly pushes against the atomization core assembly, and the elastic member is configured to push against the mouthpiece assembly to reset.

3. The atomizer according to claim 2,
   wherein the mouthpiece is capable of being driven by an external force to drive the stop sleeve to push against the slide sleeve, causing the end of the atomization core assembly to be exposed; and
   after the atomization core assembly is separated from the slide sleeve, the elastic member is configured to provide elasticity to cause the mouthpiece and the stop sleeve to reset.

4. The atomizer according to claim 3, wherein
   the liquid storage assembly further comprises a top cover;
   the top cover defines a guide cavity and comprises a stop ring, the stop ring is provided on an inner wall of the guide cavity;
   the mouthpiece assembly is received in and extends through the guide cavity, and is guided by and engaged with the guide cavity, and the other end of the stop sleeve is engaged with the stop ring for position-limiting.

5. The atomizer according to claim 4, wherein the stop sleeve comprises a sleeve body and a limitation ring configured at an outer periphery of the sleeve body, an end of the sleeve body is connected to the mouthpiece, and the limitation ring is provided at the other end of the sleeve body, and the limitation ring is engaged with the stop ring for position-limiting.

6. The atomizer according to claim 4, wherein the mouthpiece assembly further comprises a connection sleeve;
   the connection sleeve comprises a guide sleeve body and a connection sleeve body sleeving the guide sleeve body;
   the guide sleeve body and the connection sleeve body are connected via an end plate;
   the mouthpiece and the stop sleeve are embedded into two ends of the connection sleeve body;
   the guide sleeve body is guided by and engaged with the guide cavity; and
   the elastic member is elastically compressed between the end plate and the stop ring.

7. The atomizer according to claim 6, wherein the connection sleeve body comprises a first barrel section and a second barrel section, connected to each other;
   an inner diameter of the first barrel section is greater than an inner diameter of the second barrel section;
   the mouthpiece is embedded in the first barrel section, and the stop sleeve is embedded in the second barrel section.

8. The atomizer according to claim 3, wherein an end of the slide sleeve facing the atomization core assembly defines an insertion slot, and an end of the atomization core assembly is received in the insertion slot.

9. The atomizer according to claim 8, wherein the slide sleeve comprises a first slide sleeve section and a second slide sleeve section, connected to each other;
- an outer diameter of the first slide sleeve section is less than that of the second slide sleeve section;
- an end of the second slide sleeve section away from the first slide sleeve section defines the insertion slot.

10. The atomizer according to claim 3, wherein a side wall of the inner barrel defines a liquid inlet hole;
- the slide sleeve is staggered with the liquid inlet hole when the atomization core assembly is received in the receiving channel; and
- the slide sleeve is configured to cover the liquid inlet hole when the slide sleeve pushes the atomization core assembly to expose the end of the atomization core assembly.

11. The atomizer according to claim 3, wherein the stop sleeve and the slide sleeve are configured as an integral overall structure.

12. The atomizer according to claim 3, wherein the inner barrel comprises a barrel body and a ring stop portion configured at an end of the barrel body;
- the elastic member is elastically compressed between the mouthpiece and the ring stop portion; and
- the other end of the stop sleeve is arranged on a side of the ring stop portion away from the elastic member and engaged with the ring stop portion for position-limiting.

13. The atomizer according to claim 1, wherein the liquid storage assembly further comprises a base;
- an end of the inner barrel away from the mouthpiece assembly is arranged with the base;
- the base defines an embedding channel;
- the embedding channel is communicated with the slide cavity; and
- the atomization core assembly is received in the slide cavity and the embedding channel.

14. The atomizer according to claim 13, further comprising an end cap assembly, wherein the end cap assembly is connected to the base, and the end cap assembly covers the embedding channel.

15. An electronic atomization device, comprising a body assembly and an atomizer, wherein the body assembly is connected to the atomizer and is configured to supply power for the atomizer, and the atomizer comprises:
- an atomization core assembly, configured to atomize liquid;
- a liquid storage assembly, comprising an inner barrel, wherein the inner barrel defines a slide cavity for receiving the atomization core assembly;
- a mouthpiece assembly, disposed at an end of the inner barrel, wherein the mouthpiece assembly is configured to push the atomization core assembly to slide the atomization core assembly in the slide cavity, and an end of the atomization core assembly is capable of being exposed to an outside of the atomizer by being pushed by the mouthpiece assembly; and
- an elastic member;
- wherein the mouthpiece assembly comprises:
- a mouthpiece, wherein an end of the elastic member abuts against the mouthpiece;
- a stop sleeve, wherein an end of the stop sleeve is connected to the mouthpiece, and the other end of the stop sleeve is arranged with a flange configured to prevent the stop sleeve from being moved when the mouthpiece is reset; and
- a slide sleeve, received in the slide cavity and detachably connected to the atomization core assembly.

16. The electronic atomization device according to claim 15, wherein the elastic member is elastically compressed when the mouthpiece assembly pushes against the atomization core assembly, and the elastic member is configured to push against the mouthpiece assembly to reset.

17. The electronic atomization device according to claim 16,
- wherein the mouthpiece is capable of being driven by an external force to drive the stop sleeve to push against the slide sleeve, causing the end of the atomization core assembly to be exposed; and
- after the atomization core assembly is separated from the slide sleeve, the elastic member is configured to provide elasticity to cause the mouthpiece and the stop sleeve to reset.

18. The electronic atomization device according to claim 17, wherein
- the liquid storage assembly further comprises a top cover;
- the top cover defines a guide cavity and comprises a stop ring, the stop ring is provided on an inner wall of the guide cavity;
- the mouthpiece assembly is received in and extends through the guide cavity, and is guided by and engaged with the guide cavity, and the other end of the stop sleeve is engaged with the stop ring for position-limiting.

19. The electronic atomization device according to claim 18, wherein the stop sleeve comprises a sleeve body and a limitation ring configured at an outer periphery of the sleeve body, an end of the sleeve body is connected to the mouthpiece, and the limitation ring is provided at the other end of the sleeve body, and the limitation ring is engaged with the stop ring for position-limiting.

20. An atomizer, comprising:
- an atomization core assembly, configured to atomize liquid;
- a liquid storage assembly, defining a receiving channel, wherein the atomization core assembly is received in the receiving channel; and
- a mouthpiece assembly, disposed at a first end of the liquid storage assembly, wherein the mouthpiece assembly is configured to push the atomization core assembly to slide the atomization core assembly in the receiving channel, and an end of the atomization core assembly is capable of being exposed to an outside of the atomizer through a second end of the liquid storage assembly opposite to the first end; and
- an elastic member;
- wherein the mouthpiece assembly comprises:
- a mouthpiece, wherein an end of the elastic member abuts against the mouthpiece;
- a stop sleeve, wherein an end of the stop sleeve is connected to the mouthpiece, and the other end of the stop sleeve is arranged with a flange configured to prevent the stop sleeve from being moved when the mouthpiece is reset; and
- a slide sleeve, received in the receiving channel and detachably connected to the atomization core assembly.

* * * * *